United States Patent [19]

Habermeier

[11] 4,100,348
[45] Jul. 11, 1978

[54] TRIOLS CONTAINING HYDANTOIN RINGS

[75] Inventor: Jürgen Habermeier, Pfeffingen, Switzerland

[73] Assignee: Ciba-Geigy Corporation, Ardsley, N.Y.

[21] Appl. No.: 688,647

[22] Filed: May 21, 1976

[30] Foreign Application Priority Data

May 30, 1975 [CH] Switzerland .................. 6995/75

[51] Int. Cl.² ........................................ C07D 233/42
[52] U.S. Cl. ........................ 548/310; 260/22 TN; 528/73; 528/289
[58] Field of Search .............. 260/22 TN, 77.5 AQ, 260/77.5 AT, 309.5; 548/310

[56] References Cited

U.S. PATENT DOCUMENTS

| | | | |
|---|---|---|---|
| 3,679,681 | 7/1972 | Habermeier et al. | 260/309.5 |
| 3,821,243 | 6/1974 | Habermeier et al. | 260/309.5 |
| 3,893,979 | 7/1975 | Wolf et al. | 260/77.5 AQ |
| 3,925,407 | 12/1975 | Stockinger et al. | 260/309.5 |
| 3,928,289 | 12/1975 | Reilly et al. | 260/77.5 AQ |
| 3,966,683 | 6/1976 | Merten et al. | 260/309.5 |

FOREIGN PATENT DOCUMENTS 1,380,603  1/1975  United Kingdom .............. 260/309.5

*Primary Examiner*—Ronald W. Griffin
*Attorney, Agent, or Firm*—Vincent J. Cavalieri

[57] ABSTRACT

The invention relates to new triols of the formula

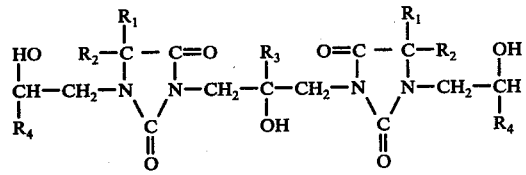

wherein $R_1$ and $R_2$ denote hydrogen, methyl, ethyl or isobutyl, or together denote tetramethylene or pentamethylene, $R_3$ denotes hydrogen or methyl, and $R_4$ denotes hydrogen or methyl or ethyl.

The new triols are useful for the manufacture of alkyl resins and polyurethanes having high glass transition temperatures.

3 Claims, No Drawings

TRIOLS CONTAINING HYDANTOIN RINGS

The invention relates to novel triols containing two hydantoin rings, to a process for producing them, and to their use for the manufacture of alkyd resins.

The manufacture of polycondensates containing ester groups, which have particularly favorable properties such as an elevated glass transition temperature and in association therewith an increased modulus of elasticity, by the addition of specific compounds such as diols, e.g., 1,1′-methylene-bis-(3-(2-hydroxyalkyl)-hydantoins), is known, e.g., from the French Pat. No. 2,029,026. Such diols are less suitable for the manufacture of polyurethanes, since on the one hand they are poorly soluble in the customary polyols and on the other hand have low compatibility with numerous polyisocyanates; furthermore they are not so well suited on account of their di-functionality. In the case of polyurethanes, the use of 4,4′-diamino-3,3′-dichlorodiphenylmethane as "cross-linking agent" for the attainment of high glass transition temperatures has proved satisfactory. However, the storage stability and the mouldability of this compound leaves much to be desired. For these reasons, and also on account of the toxic properties of this compound, a new substance was sought which does not have the stated disadvantages but which nevertheless has the desired property-enhancing effects in polyadducts or in polycondensates.

It has now been found that specific triols which contain two hydantoin rings and which correspond to the following formula I surprisingly bring about increased glass transition temperatures and modulus of elasticity in polyadducts and also in polycondensates and are suitable for polyurethane formulations, without having the disadvantages of 4,4′-diamino-3,3′-dichlorodiphenylmethane.

The invention relates to triols of formula I

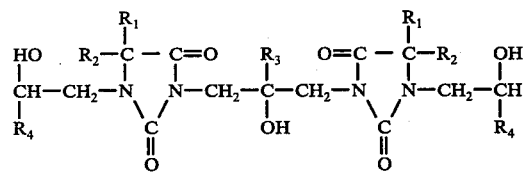

wherein $R_1$ and $R_2$ each represent hydrogen, the methyl, ethyl or isobutyl group, or together represent the tetramethylene or pentamethylene group, $R_3$ represents hydrogen or the methyl group, and $R_4$ represents hydrogen or the methyl or ethyl group.

Particularly suitable triols of formula I are those wherein $R_1$ represents the methyl or ethyl group and $R_2$ the methyl group, or $R_1$ and $R_2$ together represent the pentamethylene group, $R_3$ represents hydrogen and $R_4$ hydrogen or the methyl group; triols of formula I to be specially emphasised are those wherein $R_1$ and $R_2$ represent the methyl group, and $R_3$ as well as $R_4$ represents hydrogen.

The triols of formula I according to the invention can be produced by reacting a 1,3-bis-(hydantoinyl)-propan-2-ol of formula II

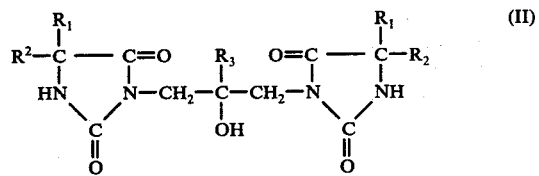

with an alkylene oxide of formula III

The starting materials, 1,3-bis-(hydantoinyl)-propan-2-ols, are preferably dissolved or suspended in an organic solvent containing no reactive groupings, and an addition is then made at 5° to 60° C of the corresponding alkylene oxide in the form of gas or liquid, or dissolved in an organic solvent. The reaction is then performed preferably at a temperature of 40° to 130° C; depending on the employed substances and conditions, the reaction has a duration of between 2 and 25 hours. The solvents used can be dioxane, tetrahydrofuran and similar solvents, especially however aprotic, strongly polar solvents such as dimethylformamide, dimethylacetamide, hexamethylphosphoric acid triamide (hexametapol), etc. The reaction is usually catalyzed by means of nucleophilic substances; catalysts preferably used as lithium chloride, potassium chloride or sodium chloride, tetramethylammonium chloride, or bases such as trimethylamine or sodium hydroxide or potassium hydroxide. Since traces of such products can be present as impurities in the solvents or in the starting materials, a separate addition of catalyst is frequently unnecessary.

The reaction can be performed also in the melt of the starting product at a higher temperature, without the addition of a solvent; it proceeds then correspondingly more rapidly.

The starting materials of formula II, which are required for the manufacturing process, can be obtained by the following working procedures:

A. 2 moles of a hydantoin of formula IV

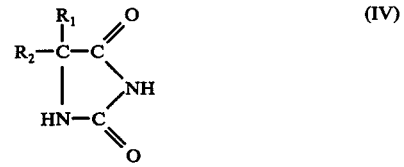

are condensed with 1 mole of 1,3-dichloropropan-2-ol, which contains in the 2-position the radical $R_3$;

B. 1 mole of a hydantoin of formula IV is reacted with 1 mole of an epihalogenohydrin in the presence of alkali to the corresponding monoglycidyl compound. To this is then added 1 further mole of the compound of formula IV;

C. 1 mole of a hydantoin of formula IV is converted with 1 mole of an epihalogenohydrin into the corresponding monohalogenohydrin compound, and this compound is converted with 1 further mole of the compound of formula IV into a compound of formula II;

D. 2 moles of a hydantoin of formula IV are condensed with 1 mole of an epihalogenohydrin with the splitting-off of hydrogen halide.

The manufacturing processes are described in more detail for example in the French Pat. No. 2,163,160 or in the British patent specification No. 1,380,603.

The novel triols of formula I are, depending on substituents, very viscous liquids, or some — in the pure state — are colorless crystalline products having melting points of between 70° and 190° C. The new products dissolve in the following solvents at elevated temperature: chlorobenzene, ethylene chloride, nitrobenzene, tetrahydrofuran, methylene chloride, chloroform, acetone, dioxane, diethylene glycol, isopropanol or polybutylene glycol ("Polymec RTM 650"); the products dissolve exceptionally well in warm water, dimethylformamide or dimethylacetamide. The products are soluble also at room temperature in the following solvents: good solubility in water, dimethylformamide and dimethylacetamide, also — but not at high concentration — in nitrobenzene, tetrahydrofuran, chloroform and methylene chloride. Furthermore, the novel products are soluble in warm methylenedi-p-phenylenediisocyanate, and very readily soluble in warm toluylidenediisocyanate ("Desmodur T 100 - RTM" Bayer) and in hexamethylenediisocyanate ("Desmodur H"). They dissolve readily in the stated diisocyanates before the cross-linking reaction occurs.

Manufacturing Examples

EXAMPLE 1

1,3-bis-(1-hydroxyethyl-5,5-dimethylhydantoin-3-yl)-propan-2-ol

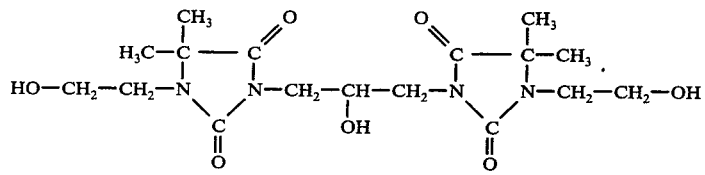

In a 6-liter glass apparatus, which is provided with a cooled dropping funnel, thermometer, intensive cooler and low-temperature cooler and stirrer, a suspension of 3120 g (10 moles) of 1,3-bis-(5,5-dimethyl-hydantoin-3-yl)-propan-2-ol (produced according to the following working instruction) in 2000 ml of N,N-dimethylformamide, to which has been added 40 g of lithium chloride, is stirred at 65° C.

There is added dropwise to this suspension in the course of 4.5 hours a solution of 880 g of ethene oxide in 1000 ml of dimethylformamide. After about half the ethene oxide solution has been added, the reaction becomes increasingly exothermic, so that the heating bath is removed; the temperature rises at the same time to 86° C. After completion of the dropwise addition and the ceasing of the exothermic reaction, the mixture is stirred for a further 4 hours at 100° C. The resulting mixture is cooled to 75° C, neutralized with 50% sulphuric acid (consumption about 25 ml) and filtered through a suction filter. The clear yellow solution is concentrated in a rotary evaporator to dryness, and then dried at 100° C/0.5 Torr to constant weight.

There is obtained 3772 g of a yellow substance solidifying in a glass-like form, which amount corresponds to a crude yield of 94.3% of theory.

To purify the crude product, it is recrystallised from 3800 ml of ethanol to give 3572.0 g of colourless crystals, corresponding to 64.3% of theory. These crystals melt at 128° - 132° C. A sample of these recrystallised from isopropanol melts at 142° - 144° C.

The elementary analysis shows the following values:

| found: | calculated: for $C_{17}H_{28}N_4O_7$ |
|---|---|
| 50.91% C | 50.99% C |
| 7.06% H | 7.05% H |
| 14.00% N | 13.99% N |

The hydroxyl number of the novel triol is determined at 410, which corresponds to 7.31 val/kg (corresponds to 97.5% of theory). The thin-layer chromatogram shows further that the product is homogeneous (eluant: ethyl acetate/cyclohexane/acetic acid = 50:30:20). Also the proton-magnetic resonance spectrum is in agreement with the given formula.

Manufacture of 1,3-bis-(5,5-dimethylhydantoinyl-3)-propan-2-ol

There is placed into a 4-liter glass apparatus fitted with stirrer, thermometer and intensive cooler at room temperature a mixture of 520 g (3.83 moles) of glycerol dichlorohydrin (1,3-dichloropropan-2-ol) (95% according to gas chromatogram), 981 g (7.66 moles) of 5,5-dimethylhydantoin (99.5%), 582 g (4.21 moles) of finely pulverised anhydrous potassium carbonate and 960 ml of commercial dimethylformamide. Whilst the mixture is slowly stirred, the pasty mixture is heated to 120° C, whereupon the mixture becomes thinly liquid. There immediately commences an exothermic reaction with an intense evolution of $CO_2$. The heating bath is removed and the paste, which is again becoming thick, is vigorously stirred. After removal of the heating bath, the temperature rises to 124° - 126° C. After about 25 - 30 minutes the exothermic reaction subsides and the temperature of the reaction mixture falls to 116° C. The mixture is stirred for a further 5 hours at 126° C to complete the reaction, and the hot reaction mixture is filtered through a porcelain suction filter to separate the potassium chloride.

The mixture is concentrated in a rotary evaporator at 70° - 80° C in a water-jet vacuum to dryness; the product is thus obtained as a clear, slightly yellow-colored melt which spontaneously crystallizes out at elevated temperature. In order to remove volatile constituents, the product is dried at 90° C and 0.2 Torr to constant weight.

There is obtained 1212.6 g of a colorless to pale yellow crude crystallizate (theory: 1196.5 g), which melts at 142° C ("Mettler FP 51"). This crude product still contains some potassium chloride and unreacted starting products.

For purification, the crude product can be recrystallized from 550 g of water, whereupon there is obtained 716.5 g (corresponding to 60.6% of theory, relative to the employed dimethyl-hydantoin) of purified product.

EXAMPLE 2

1,3-bis-[1-(2-hydroxy)-propyl-5,5-dimethylhydantoin-3-yl]-propan-2-ol

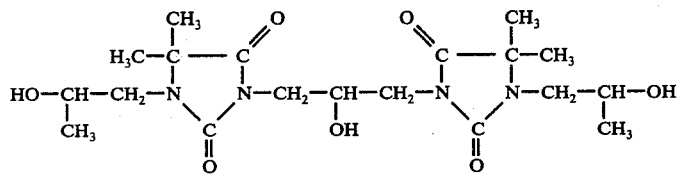

5.0 g of potassium chloride is added to 624.8 g (2.0 moles) of the starting material used in Example 1, and the whole is then dissolved at 65° C with stirring in 1500 ml of dimethylformamide. In the course of 4 hours, there is added dropwise, with gentle stirring, 290.4 g (5.0 moles) of propene oxide. After this dropwise addition, stirring is maintained for a further 12 hours at 80° C, and the mixture is then cooled to room temperature. The pale yellow reaction mixture is filtered, concentrated by evaporation to dryness and then dried at 100° C/0.3 Torr to constant weight. There is obtained 790.0 g (corresponding to 92.2% of theory) of a light-yellow brittle resin, which for most purposes requires no further purification. The elementary analysis for this product shows the following values:

| found: | calculated: for $C_{19}H_{32}N_4O_7$ |
|---|---|
| 53.0 % C | 53.26 % C |
| 7.6 % H | 7.53 % H |
| 13.1 % N | 13.08 % N |

The gel-permeation chromatographical analysis shows by the presence of only one peak that the new triol is molecular-homogeneous; furthermore, the molecular weight found agrees with the calculated value. The proton-magnetic resonance spectrum is in agreement with the given formula.

EXAMPLE 3

1,3-bis-(1-hydroxyethyl-5,5-pentamethylenehydantoin-3-yl)-propan-2-ol

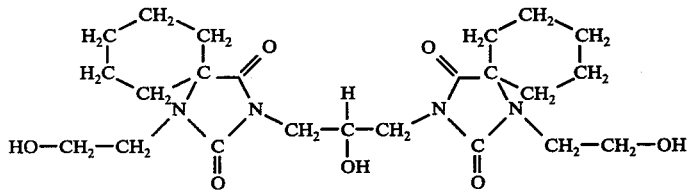

In an apparatus such as that described in Example 1, a clear solution of 392.5 g (1 mole) of 1,3-bis-(5,5-pentamethylenehydantoin-3-yl)-propan-2-ol in 2000 ml of dimethylformamide is stirred at 65°-70° C. There is added dropwise to this solution, after the addition of 5 g of lithium chloride, a solution of 105 g (2.4 moles) of ethylene oxide in 250 ml of dimethylformamide in the course of 1.5 hours. The temperature is subsequently raised within a period of 60 minutes to 92° C, and this temperature is maintained for 7 hours. The mixture is then cooled to room temperature and rendered neutral with 16 ml of 50% sulphuric acid. After filtration, the solution is concentrated in a rotary evaporator, whereby the temperature is raised to 140° C. The residue is afterwards dried at 0.2 Torr until the weight remains constant. There is obtained 409.5 g (corresponding to 85% of theory) of a glass-like, hard-brittle substance having a slightly yellowish color.

A sample of this substance is firstly dissolved in the three-fold amount of n-butanol and then precipitated with ether. The precipitate is recrystallized from ethanol/water (7:3).

There are obtained colorless crystals which melt at 112°-114° C. According to H-NMR spectrum, the product is consistent with the above formula. The microanalysis, too, is in agreement therewith:

| found: | calculated: for $C_{23}H_{36}N_4O_7$: |
|---|---|
| 7.55 % H | 7.55 % H |
| 11.90 % N | 11.66 % N |

Application Examples

EXAMPLE A (a) To 65.0 g of polybutylene glycol 650 (mean molecular weight of 650), from which traces of water have been removed by heating in vacuo at 120° C for 3 hours, there is added, with stirring, 35.3 g of toluylene-1,4-diisocyanate ("Desmodur T 100," registered trademark) to thus produce a pre-adduct. After the exothermic reaction has subsided, 26.7 g of the triol produced according to Example 1 is added as "cross-linking agent"; this addition is made by introducing into the pre-adduct at about 120° C a melt, at about 140° C, of the cross-linking agent according to the invention. After the addition of the cross-linking agent, the container is briefly evacuated and the mixture is subsequently poured into aluminum moulds of 4 mm wall thickness, preheated to 100° C. Curing is effected in 2.5 hours at 150° C.

(b) For comparison, an analogous pre-adduct of polybutylene glycol 650 and toluylene-1,4-diisocyanate is produced, and to this is added an equivalent amount of a commercial cross-linking agent, namely trimethylol propane (8.93 g), and this mixture is then treated in a manner identical to that described under (a).

Both casting-resin mixtures in the cured condition give clear colorless test sheets. It is shown however that the sheet produced with the cross-linking agent of the invention has a significantly better hardness:

Shore hardness
(DIN 53 505), Type A
according to the invention (a) 87.7
comparison (b) 70.7.

EXAMPLE B

A pre-polymer is produced in 30 minutes at 110° C, with stirring, from 100 g of a low-molecular ester having terminal hydroxyl groups, which is derived from adipic acid and ethylene glycol with OH-number 55 ("Desmophen 2000," registered trademark) and which has previously been freed from traces of water by heating (3 hours at 130° C) in vacuo (0.5 Torr), and 49.5 g of 4,4'-diisocyanato-diphenylmethane ("Desmodur 44 V" (registered trademark).

Into this pre-polymer, still at about 100° C, there is stirred a mixed melt of 50 g of "Desmophen 2000" and 29.8 g of the triol produced according to Example 1 (dissolved at 150° C until clear and then cooled to about 120° C).

This casting resin mixture is poured into aluminum moulds of 4 mm wall thickness, and cured in the course of 5 hours at 140° C. The following data were determined by tests on the clear transparent, light-brown-coloured test specimen (color of "Desmodur 44"):
tensile strength (DIN 53455): 32.2 kp/mm² = 3.17 N/mm,
elongation at break (DIN 53455): 162 –372372 %,
hardness: Shore, Type A: 72.4.

EXAMPLE C (a) A pre-polymer is produced from 70 g of the polyester used in Example B and 34 g of toluylenediisocyanate (see Example A) in a manner similar to that described in Example B.

This pre-polymer is mixed at 100° C with a homogeneous mixture of 13 g of the triol produced according to Example 1 and 30 g of the above polyester (mixed at 160° C and cooled to 110° C), and the resulting mixture is cast and cured as described in Example B.

(b) The procedure is carried out in a manner analogous to that described under (C, a) with the exception that the triol according to the invention is replaced by the 4,4'-diamino-3,3'-dichlorodiphenylmethane representing the prior art, in an equivalent amount (8.7 g). Processing and curing are performed as described under (C, a).

RESULTS (a) product of the invention
hardness, Shore, type A 86.5
hardness, Shore, type D 38.1
water absorption ($4^d/20°$) 1.60%
(b) comparison product
hardness, Shore, type A 85.0
hardness, Shore, type D 37.0
water absorption ($4^d/20°$) 2.32%.

This comparison shows that — irrespective of the toxicological questionability of diaminodichlorodiphenylmethane — the triol of the invention gives with analogous curing with analogous pre-polymers at least the same Shore hardnesses. Furthermore, there is obtained in this Example with the use of the cross-linking agent of the invention a lower value of water absorption.

The procedures just as described in Example B or C can be carried out with other diisocyanates, such as 1,5-diisocyanatonaphthalene. With the use however of hexamethylene-diisocyanate ("Desmodur H"), of the "trimer" of hexamethylene-diisocyanate ("Desmodur N") and of cycloaliphatic isophorone-diisocyanate, the employment of traces of catalysts is advisable (e.g., dibutyltin dilaurate, etc.).

I claim:
1. A triol of formula I

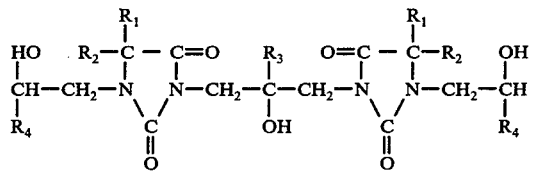

wherein $R_1$ and $R_2$ each denote hydrogen, methyl, ethyl or isobutyl, or together denote tetramethylene or pentamethylene, $R_3$ denotes hydrogen or methyl, and $R_4$ denotes hydrogen or methyl or ethyl.

2. A triol according to claim 1 of formula I, wherein $R_1$ denotes methyl or ethyl and $R_2$ denotes methyl, or $R_1$ and $R_2$ together denote pentamethylene group, $R_3$ represents hydrogen and $R_4$ hydrogen or the methyl group.

3. A triol according to claim 1 of formula I, wherein $R_1$ and $R_2$ represent the methyl group, and $R_3$ and $R_4$ represent hydrogen.

* * * * *